US00PP10962P

United States Patent [19]

Walden

[11] Patent Number: Plant 10,962

[45] Date of Patent: Jun. 15, 1999

[54] SHRUB ROSE PLANT NAMED 'JACINA'

[75] Inventor: John K. Walden, Thousand Oaks, Calif.

[73] Assignee: Bear Creek Gardens, Inc., Medford, Oreg.

[21] Appl. No.: 08/943,394

[22] Filed: Oct. 3, 1997

[51] Int. Cl.[6] ..... A01H 5/00

[52] U.S. Cl. ..... Plt./107

[58] Field of Search ..... Plt./1, 22, 27, Plt./28, 7.1, 9, 10, 107, 102, 108

[56] References Cited

U.S. PATENT DOCUMENTS

P.P. 678 4/1946 Lammerts ..... Plt./26
P.P. 4,282 7/1978 Weeks ..... Plt./18
P.P. 5,734 5/1986 Warriner ..... Plt./26

OTHER PUBLICATIONS

Modern Roses 9, 1986, The American Rose Society, Shreveport, Louisiana, P.A. Haring, editor, pp. 52–53, 142–143.

Plant Patent Directory, 1990, The American Association of Nurserymen, p. 0015 (alphabetical listing of denominations).

*Primary Examiner*—Howard J. Locker
*Attorney, Agent, or Firm*—Klarquist Sparkman Campbell Leigh & Whinston, LLP

[57] ABSTRACT

A continuously flowering shrub rose plant with five petaled flowers of deep pink color, the plant having a uniform, rounded growth habit, a resistance to black spot, and tolerance of powdery mildew and rust.

1 Drawing Sheet

The present invention relates to a new and distinct variety of rose plant of the shrub class which was originated by me by crossing the variety China Doll, U.S. Plant Pat. No. 678, with the variety MORchari, U.S. Plant Pat. No. 5,975.

The primary objective of this breeding was to produce a new rose variety having high flower production, full compact habit, disease resistance, pink to red in color, and fragrance. The objective was substantially achieved, along with other desirable improvements, as evidenced by the following unique combination of characteristics that are outstanding in the new variety and that distinguish it from its parents, as well as from all other varieties of which I am aware:

1. Superior continuous bloom;
2. Full, compact, rounded habit of growth;
3. Resistance to blackspot;
4. Tolerance of powdery mildew and rust;
5. Deep pink color;
6. Light, spicy fragrance.
7. A deep pink, five petaled flower, its parent 'China Doll' having a slightly fragrant, medium pink flower with 20–26 petals, and 'MORchari,' a very fragrant, lavender to purple flower of 40 plus petals. JACina's mature plant is 28–30 inches in height whereas China Doll grows to about 18" in height and 'MORchari' to between 24–28" in height.

Asexual reproduction of this new variety by cutting propagation, as performed at Wasco and Somis, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—China Doll (U.S. Plant Pat. No. 678).

*Pollen parent.*—MORchari (U.S. Plant Pat. No. 5,975).

Classification:

*Botanical.*—Rosa hybrida.

*Commercial.*—Shrub.

FLOWER

Observations made from specimens grown in a garden environment at Somis and Wasco, Calif. and Baton Rouge, La. from 1991–1997.

Blooming habit: Continuous.

Bud:

*Size.*—One-half inch long when the petals start to unfurl.

*Form.*—The bud form is short, pointed ovoid.

*Color.*—When sepals first divide, bud color is Red-purple Group 58A. When half blown, the upper sides of the petals are Red-purple Group 63A; and the lower sides of the petals are Red-purple Group 63B.

*Sepals.*—Color: Yellow-green group 144A. Surface texture: Rough, with very small glandular structures. There are three normally appendaged sepals. There are two unappendaged sepals with hairy edges.

*Receptacle.*—Color: Yellow-green Group 144A. Shape: Apple. Size: Small, slender (3/16" long×1/8" wide). Surface: Smooth.

*Pedicel.*—Length: Short (11/16" to 13/16"). Surface: Glandular. Color: Yellow-green Group 146D. Strength: Erect, slender.

*Peduncle.*—Length: About 1½". Color: Near Greyed-red Group 178A, with reddish hue where exposed to sunlight. Strength: Erect, but not rigid.

*Opening.*—Quickly, to a flat to slightly cupped flower with undulating petals.

Bloom:

*Size.*—Small. Average open size is 1½ to 1¾ inches.

*Borne.*—In pyramidal clusters of 3–7 blooms.

*Stems.*—Short, (7–10") normal strength.

*Form.*—When first open: Cupped. Permanence: Flattens; outer petal edges curl slightly.

*Petalage.*—Number of petals under normal conditions: 5.

*Color.*—The upper sides of the petals are Red-purple Group 63A. The reverse sides of the petals are Red-purple Group 63B. The petals shade to Red-purple Group 62D toward their base with a ¼" white crescent at the petal base. The major color on the upper side is Red-purple Group 63A.

*Variegations.*—None other than crescent at petal base.

*Discoloration.*—The general tonality at the end of the first day: Red-purple Group 63A. At the end of the third day: Red-purple Group 67A.

*Fragrance.*—Slight, spicy.

Petals:

*Texture.*—Thin.

*Shape.*—Oval.

*Form.*—Flat, tips slightly recurved.

*Arrangement.*—Regularly arranged, with few to no petaloids in the center. Petaloids, when present, are small (¼") mixed in with or around the anthers.

*Persistence.*—Drop off cleanly.

*Lastingness.*—On the plant: Long (5–7 days). As a cut flower: Not tested.

Reproductive parts:

*Anthers.*—Size: Small. Quantity: Many. Color: Yellow. Arrangement: Regular around styles.

*Filaments.*—Color: White.

*Pollen.*—Color: Gold yellow.

*Styles.*—Color: Greenish white to red.

*Stigmas.*—Color: Yellow.

*Form.*—Bush. Mature plant is 28–30" in height and about 30" in width.

*Growth.*—Medium; upright; branching; compact.

*Foliage.*—Number of leaflets on normal mid-stem leaves: 7.

*Size.*—Small (3¼" in length×2" width).

*Quantity.*—Abundant.

*Color.*—New foliage: Upper surface: Yellow-green Group 146A. Lower surface: Yellow-green Group 146C. Old foliage: Upper surface: Green Group 137A. Lower surface: Green Group 137C.

*Shape.*—Elliptic.

*Texture.*—Upper side: Leathery. Non-glossy.

*Edge.*—Serrated.

*Serration.*—Single, small.

*Petiole rachis.*—Color: Green Group 137D.

*Petiole underside.*—With prickles.

*Stipules.*—Long; serrated.

*Disease resistance.*—Resistant to blackspot under normal growing conditions at Baton Rouge, La. Tolerant of powdery mildew and rust in Wasco and Somis, Calif.

Wood:

*New wood.*—Color: Greyed-orange Group 166A. Bark: Smooth.

*Old wood.*—Color: Yellow-green Group 144A. Bark: Smooth.

Prickles:

*Quantity.*—On main canes from base: Ordinary to few. On laterals from main canes: Ordinary.

*Form.*—Short (⅛" to 3/16"); hooked downward.

*Color when young.*—Red.

Small prickles:

*Quantity.*—On main stalks: None. On laterals: None.

I claim:

1. A new and distinct variety of rose plant of the shrub class, substantially as herein shown and described, characterized particularly as to novelty by the unique combination of its continuous flowering of five petaled pink flowers having a light, spicy fragrance on a compact, very healthy rose plant having a uniform, rounded growth habit, and a resistance to blackspot and tolerance of powdery mildew and rust.

* * * * *

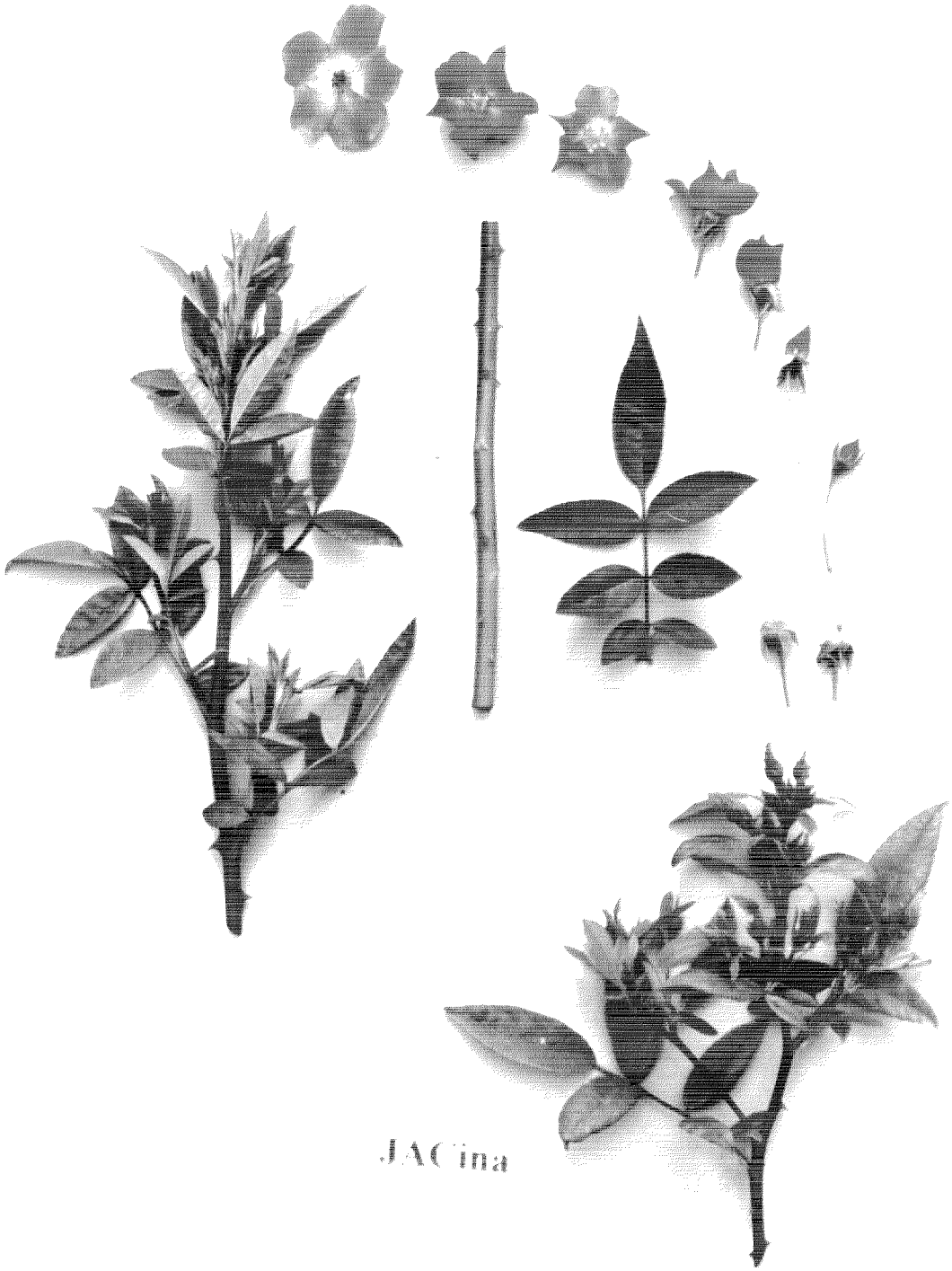
JACina

UNITED STATES PATENT AND TRADEMARK OFFICE

CERTIFICATE OF CORRECTION

PATENT NO. : Plant 10,962

DATED : June 15, 1999

INVENTOR(S) :

John K. Walden

It is certified that error appears in the above-identified patent and that said Letters Patent is hereby corrected as shown below:

Column 2/Line 35, after "Erect, but not rigid." insert – Surface: Some glands.

Column 3/Between Lines 31 and 32, missing heading: insert—Plant--.

Signed and Sealed this

Fifteenth Day of May, 2001

Nicholas P. Godici

*Attest:*

NICHOLAS P. GODICI

*Attesting Officer*

*Acting Director of the United States Patent and Trademark Office*